(12) United States Patent
Togawa et al.

(10) Patent No.: US 7,767,466 B2
(45) Date of Patent: Aug. 3, 2010

(54) SAMPLE FILTERING METHOD USING SAMPLE COLLECTING CONTAINER, JIG AND SAMPLE COLLECTING CONTAINER

(75) Inventors: Katsuya Togawa, Shunan (JP); Hironobu Isogawa, Tokyo (JP)

(73) Assignees: Sekisui Medical Co., Ltd., Tokyo (JP); I-Design Co., Ltd., Osaka (JP); Nittobo Medical Co., Ltd., Tokyo (JP)

( * ) Notice: Subject to any disclaimer, the term of this patent is extended or adjusted under 35 U.S.C. 154(b) by 1252 days.

(21) Appl. No.: 10/551,437
(22) PCT Filed: Apr. 22, 2004
(86) PCT No.: PCT/JP2004/005783
§ 371 (c)(1), (2), (4) Date: Sep. 29, 2005
(87) PCT Pub. No.: WO2004/096046
PCT Pub. Date: Nov. 11, 2004

(65) Prior Publication Data
US 2006/0199275 A1  Sep. 7, 2006

(30) Foreign Application Priority Data
Apr. 25, 2003  (JP) .............................. 2003-122763

(51) Int. Cl.
*B01L 11/00* (2006.01)
*G01L 1/18* (2006.01)
(52) U.S. Cl. .................. 436/177; 422/101; 422/102
(58) Field of Classification Search ................. 436/177; 422/101, 102; 210/745
See application file for complete search history.

(56) References Cited
U.S. PATENT DOCUMENTS
2,833,281 A * 5/1958 Krug ........................... 604/406
3,837,376 A * 9/1974 Brown et al. ................... 141/1

(Continued)

FOREIGN PATENT DOCUMENTS

| JP | 4-020856 A | 1/1992 |
| JP | 7-327963 A | 12/1995 |
| JP | 11-239574 A | 9/1999 |
| JP | 11-290297 A | 10/1999 |
| JP | 2000-074910 A | 3/2000 |
| JP | 2001-056336 A | 2/2001 |
| JP | 2001-194365 A | 7/2001 |
| JP | 2001-321365 A | 11/2001 |

(Continued)

OTHER PUBLICATIONS

International Search Report.

*Primary Examiner*—Robert J Hill, Jr.
*Assistant Examiner*—Dwan A Gerido
(74) *Attorney, Agent, or Firm*—Cheng Law Group, PLLC

(57) ABSTRACT

A method for filtrating liquid sample such as blood or the like with a filter member utilizing inner vacuum, the same enabling completion of filtration without removing a stopper, and superior in safety and being free from contamination.

In collecting and filtrating the liquid sample using a sample collection vessel 1, in which a sample-collecting part 3 containing a filter member 4 is inserted in a vacuumed sample-storing part 2, the sample storing part 2 and sample-collecting part 3 are air-tightly sealed with a stopper 5, the liquid sample such as blood or the like collected in the sample-collecting part 3 is filtrated by the filter member 4. When the filtration stops, a hollow needle 12 is pierced through the stopper 5 and thus the sample-collecting part 3 is communicated with atmosphere, thereby the pressure in the sample-collecting part 3 being enhanced upper than in atmosphere to enable the filtration again.

4 Claims, 9 Drawing Sheets

U.S. PATENT DOCUMENTS

| | | | | |
|---|---|---|---|---|
| 5,213,765 A | * | 5/1993 | Kasai et al. | 422/101 |
| 5,308,506 A | * | 5/1994 | McEwen et al. | 210/745 |
| 5,624,554 A | * | 4/1997 | Faulkner et al. | 210/232 |
| 2002/0177772 A1 | * | 11/2002 | Altman et al. | 600/431 |
| 2004/0013575 A1 | * | 1/2004 | Stevens et al. | 422/102 |

FOREIGN PATENT DOCUMENTS

| | | |
|---|---|---|
| JP | 2002-277357 A | 9/2002 |
| JP | 2004-099081 A | 4/2004 |

* cited by examiner (a)

(b)

SAMPLE FILTERING METHOD USING SAMPLE COLLECTING CONTAINER, JIG AND SAMPLE COLLECTING CONTAINER

FIELD OF THE INVENTION

The present invention relates to methods for filtering a sample using a sample collecting container capable of collecting and filtering a liquid sample such as blood, and to sample collecting containers, and more specifically, to a sample filtering method using a sample collecting container, the sample collecting container being depressurized in advance and filtering a collected sample by pressure difference, a jig and a sample collecting container.

BACKGROUND ART

Conventionally, a variety of noncentrifugal blood collection tubes have been proposed wherein a blood sample is collected by a vacuum blood collection needle by utilizing reduced pressure in a container and the blood is filtered through a filter member accommodated in the container. Such blood collection tubes are disclosed, for example, in Japanese Unexamined Patent Publication No. 2002-277357, Japanese published Patent No. 3015854, Japanese Unexamined Patent Publication No. 11-290297 (1999), Japanese Unexamined Patent Publication No. 4-20856 (1992) and Japanese Unexamined Patent Publication No. 2001-321365.

In a conventional noncentrifugal sample collecting container, a plug member is pierced with a vacuum blood collection needle and blood is collected using reduced pressure. Then the collected blood is filtrated through a filter member located in the sample collecting container or combined with the sample collecting container. In this case, the vacuum blood collection needle is removed after completion of the blood collection. The collected blood passes through the filter member owing to the reduced pressure remaining in the lower part of the filter member, namely in the part into which filtrated blood is to be stored. In brief, blood is filtrated by a pressure difference between upside and downside of the filter member.

However, when the pressures of upside and downside of the filter member reach equilibrium, the driving force for filtration is cancelled so that the filtration stops. For this reason, in order to promote the filtration, it was conventionally necessary to make the upside of the filter member to be atmospheric pressure by detaching the plug member above the filter member to generate a pressure difference between downside and upside of the filter member. In this procedure, however, since the plug member of sample collecting container storing a collected blood sample need to be detached, the operator is susceptible to infection by adhesion of blood. In addition, when the plug member is removed from the sample collecting container, the space over the filter member is widely exposed to the exterior to lead a risk of contamination by foreign matters.

A sample collecting container disclosed in Japanese Unexamined Patent Publication No. 11-290297 (1999) has such a structure that an inner tube provided with a filter member in a lower part is hermetically inserted into an outer tube, and filtration is promoted by lowering the pressure in a space under the filter member in the outer tube by moving the inner tube in the direction of removing it from the outer tube. In this structure, however, the driving force required for filtration is inadequate only by the pressure difference obtainable by the above operation, so that filtration may possibly stop during the filtration process.

In a sample collecting container disclosed in Japanese Unexamined Patent Publication No. 4-20856 (1992), a collection container for collecting a filtered sample, which is sealed with a plug and depressurized in advance, and a sample collecting container in which blood has been collected are connected via a filter member, and the blood sample in the sample collecting container is allowed to pass through the filter member by the reduced pressure in the collection container for collecting a filtered sample. In this approach, the degree of depressurization in the sample collecting container is relatively higher, however, there is still fear that filtration stops during the filtration process.

DISCLOSURE OF THE INVENTION

In consideration of the current state of conventional arts, it is an object of the present invention to provide a sample filtering method using a sample collecting container, a jig and a sample collecting container, the sample collecting container capable of not only securely completing filtration of a sample such as blood through a filter member using reduced pressure in the container, but also eliminating an operation that may cause infection by blood such as removing a plug member so as to complete the filtration, as well as achieving excellent safety.

In a first aspect of the present invention, there is provided a sample filtering method using a sample collecting container including a sample collection part storing a collected liquid sample and having an opening; a plug member provided so as to hermetically seal the opening; a filter member provided in the sample collection part, for filtering the sample collected in the sample collection part; and a sample storage part for storing a sample filtered by the filter member, the internal pressure thereof being reduced in advance, wherein after collecting a sample in the sample collection part using a vacuum blood collection needle, the sample is filtered by pressure difference between the sample collection part and the sample storage part, while the internal pressure of the sample collection part is increased by allowing the sample collection part to communicate with the exterior by piercing the plug member with a communication needle having a communication flow channel.

In one specific aspect of the first aspect of the invention, the communication needle is a hollow needle.

In other specific aspect of the first aspect of the invention, the communication needle has a communication groove formed on its outer surface and the communication groove extends from a needlepoint toward an end opposite to the needlepoint.

In a second aspect of the present invention, there is provided a sample collection jig to be used for establishing communication between inside and outside of the a sample collecting container sample collecting container having a sample collection part storing a collected liquid sample and having an opening, and a plug member provided so as to hermetically seal the opening. The jig comprises: a communication needle having a communication flow channel extending from the side of a needlepoint to the other end opposite to the needlepoint; a gripping portion attached to the side of the other end of the communication needle; a skirt portion extending in the axial direction of the communication needle from the gripping portion; and at least one vane provided on the side of the needlepoint of the communication needle.

In one specific aspect of the second aspect of the invention, the communication needle is a hollow needle.

In other specific aspect of the second aspect of the invention, the communication needle has a communication groove formed on its outer surface and the communication groove extends from a needlepoint toward an end opposite to the needlepoint.

In a third aspect of the present invention, there is provided a sample collecting container capable of filtering a liquid sample, comprising: a sample collection part having an opening and storing a collected liquid sample; a plug member provided so as to hermetically seal the opening; a filter member provided in the sample collection part, for filtering the sample collected in the sample collection part; and a sample storage part for storing the sample filtered by the filter member, the sample collection part, the filter member and the sample storage part being hermetically connected with each other, the internal pressure of sample storage part being reduced in advance, wherein the plug member has a through hole for establishing communication between the sample collection part and the exterior, and the through hole is hermetically sealed by a removable sealing member on the outer surface of the plug member.

The above plug member may be pressed into the aforementioned opening, and in such a case, the plug member can be realized by a common plug formed of rubber, elastomer or the like. It is to be noted, however, "plug member" used in the first to the third aspects of the invention is not limited to that having a form to be pressed into an opening insofar as it can hermetically seal the opening. For example, the plug member may be formed into a closing member from a sheet or a molded material made of a flexible material. Also in the case of a plug member formed from a sheet or the like member, the plug member can be formed with a through hole for allowing communication between the sample collection part and the exterior and the through hole can be hermetically sealed with a removable sealing member on the outer surface of the plug member.

In one specific aspect of the third aspect of the invention, the sealing member is a sheet affixed to the outer surface of the plug member so as to cover the outer surface where the through hole of the plug member is open.

In other specific aspect of the third aspect of the invention, the sealing member is a plug press-fitted into the through hole.

In a fourth aspect of the present invention, there is provided a sample collecting container capable of filtering a liquid sample, comprising: a sample collection part having an opening and storing a collected liquid sample; a plug member pressed into the opening so as to hermetically seal the opening; a filter member provided in the sample collection part, for filtering the sample collected in the sample collection part; and a sample storage part for storing the sample filtered by the filter member, the sample collection part, the filter member and the sample storage part being hermetically connected with each other and the internal pressure of sample storage part being reduced in advance, wherein an open through hole is formed in a part of inner surface of the sample collection part that is in contact with the plug member, and a flow channel is formed in a part of outer surface of the plug member contacting the inner surface of the sample collection part, the flow channel establishing communication between the through hole and the interior of the sample collection part when its circumferential position is brought into coincidence with the through hole.

In a fifth aspect of the present invention, there is provided a sample collecting container capable of filtering a liquid sample, comprising: a sample collection part having an opening and storing a collected liquid sample; a plug member provided so as to hermetically seal the opening; a filter member provided in the sample collection part, for filtering the sample collected in the sample collection part; and a sample storage part for storing a sample filtered by the filter member, the sample collection part, the filter member and the sample storage part being hermetically connected with each other and the internal pressure of sample storage part being reduced in advance, wherein an open through hole is formed in a part of inner surface of the sample collection part that is in contact with the plug member, and a flow channel is formed in the plug member in such a manner that when the plug member is drawn out from the sample collection part while keeping hermetical sealing between the plug member and the inner surface of the sample collection part, one end of the flow channel is opposite to the through hole and the other end of the flow channel is open in the sample collection part.

BEST MODE FOR CARRYING OUT THE INVENTION

The present invention can be more clearly understood from the following concrete embodiments with reference to the attached drawings.

Figure 1:
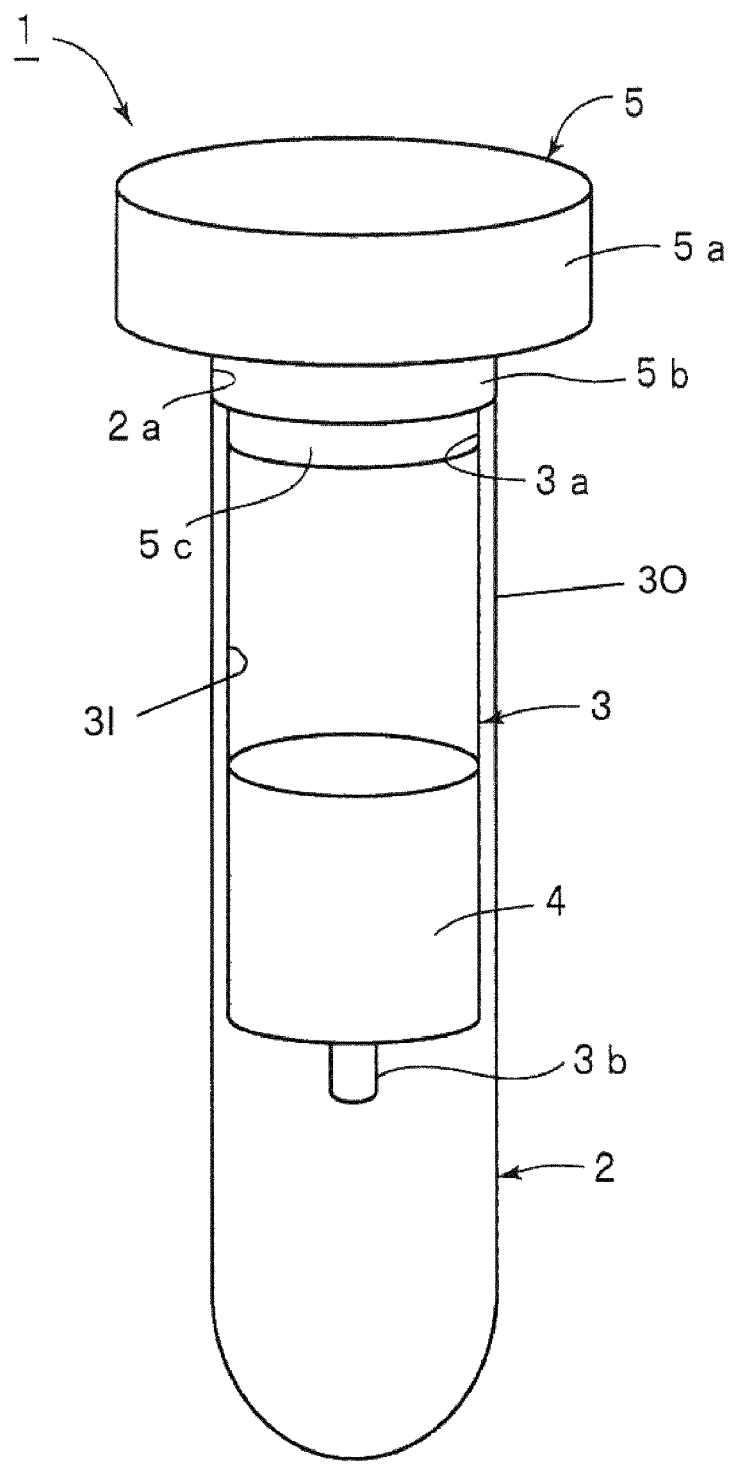
FIG. 1 is a schematic perspective view of a sample collecting container used in a sample filtering method of a first embodiment of the present invention.

FIG. 1 is a perspective view of a sample collecting container used in a sample filtering method according to a first embodiment of the present invention.

A sample collecting container 1 has a sample storage part 2 formed of a cylindrical outer ring having a bottom. At an upper end of the sample storage part 2 is formed an opening 2a.

In the present embodiment, the sample storage part 2 represents a part that stores a filtered sample. The sample storage part 2 accommodates a sample collection part 3. The sample collection part 3 used herein refers to the part where a sample before filtration is collected.

In the present embodiment, the sample collection part 3 is formed of a generally cylindrical inner tube. The sample collection part 3 is formed with an opening 3a at its upper end and has an inner surface (3I) and outer surface (3O). The sample collection part 3 is also formed with a sample dropping part 3b for filtering the filtered sample at its lower end. The sample dropping part 3b is formed integrally with the sample collection part 3 so that it projects downward from the bottom surface of the sample collection part 3.

The sample dropping part 3b has a hollow channel through which the filtered sample drops.

The sample collection part 3 accommodates a filter member 4. The filter member 4 is formed of an appropriate filter material for removing solid substances in the sample. As such a filter material, fiber assembly, microparticles and the like can be exemplified.

The sample storage part 2 and the sample collection part 3 can be formed of, for example, a synthetic resin, glass or the like.

The openings 2a and 3a of the sample storage part 2 and the sample collection part 3 are hermetically sealed with a plug member 5. Specifically, the plug member 5 has a gripping portion 5a, a larger-diameter portion 5b projecting downward from the bottom surface of the gripping portion 5a, and a smaller-diameter portion 5c having a relatively small diameter and projecting downward from the bottom surface of the larger-diameter portion 5b. The smaller-diameter portion 5c is pressed into the opening 3a of the sample collection part 3, whereby the opening 3a of the sample collection part 3 is hermetically sealed and the sample collection part 3 is fixed to the plug member 5. The larger-diameter portion 5b is pressed into the opening 2a of the sample storage part 2, whereby the opening 2a of the sample storage part 2 is hermetically sealed and the sample storage part 2 is fixed to the plug member 5.

The interior of the sample storage part 2 is depressurized to a pressure of 1 to 90 kPa in advance.

Therefore, when blood is collected as a sample, blood can be collected into the sample collection part 3 using the reduced pressure in the sample collecting container 1 by piercing the plug member 5 with a known vacuum blood collection needle. After collecting the blood, the vacuum blood collection needle is removed from the plug member 5.

The plug member 5 is formed of an elastomer or rubber, such as styrene-based elastomers, ester-based elastomers, urethane-based elastomers, butyl rubber, halogenated butyl rubber and natural rubber, for example. Therefore, the hole created by piercing with the vacuum blood collection needle is closed after removal of the vacuum blood collection needle, and the depressurized state in the sample collecting container 1 is kept for a certain period of time. More specifically, while the degree of depressurization in the sample collecting container 1 decreases as the time elapses, the internal space of the sample collection part 3 over the filter member 4 is continuously kept at higher pressure than the space under the filter member 4 of the sample storage part 2.

Therefore, owing to the remaining pressure in the sample storage part 2, blood is filtered through the filter member 4. As described in the section of related arts, also in this case, filtration stops when the pressures of upside space and downside space of the filter member 4 reach equilibrium in the sample collecting container 1.

In order to solve this problem, conventionally, filtration was completed by removing the plug member 5 to open the space over the filter member 4 to air, and again giving a pressure difference between the interior of the sample storage part 2 and the space over the filter member 4. In this approach, however, it is possible that the operator will come into contact with blood and is infected by it.

Figure 2:
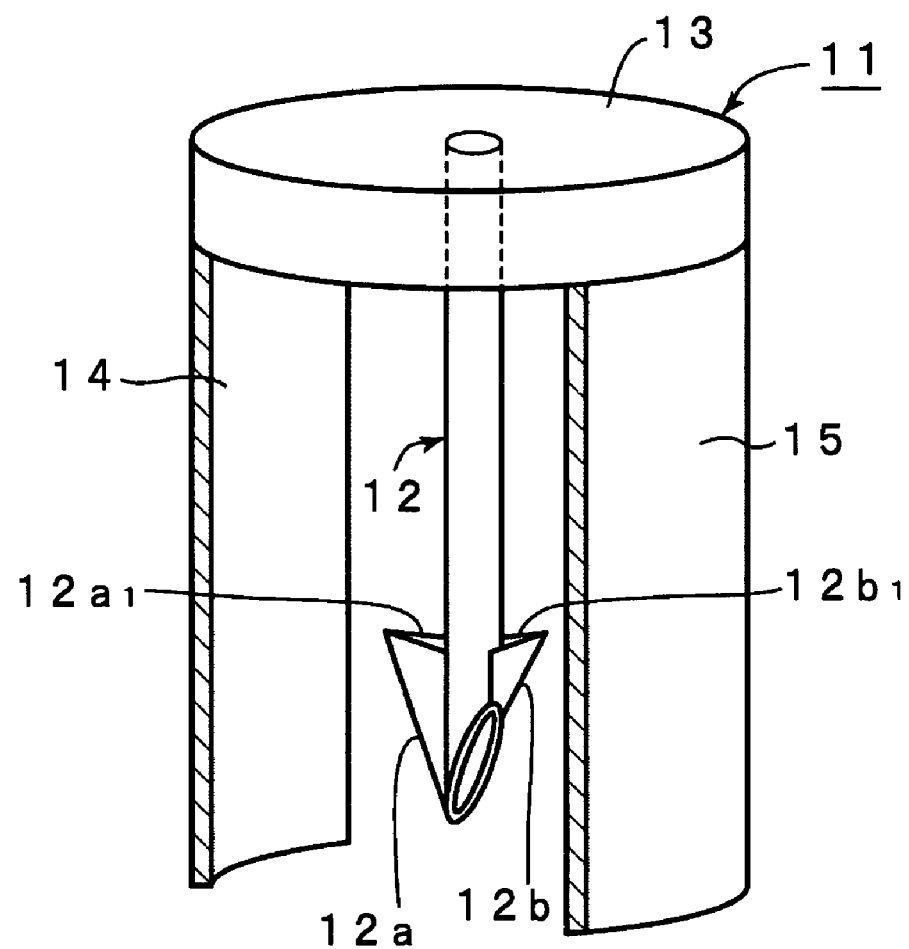
FIG. 2 is a perspective view of a jig used in a sample filtering method of the first embodiment of the present invention.

In contrast to this, according to the filtering method of the present embodiment, a jig 11 illustrated in FIG. 2 is used to establish communication between the internal space of the sample collection part 3 and the atmosphere, whereby a pressure difference is given between the internal space of the sample collection part 3 and the internal space of the sample storage part 2.

The jig 11 has a pointed hollow needle 12 as a communication needle. Near the upper end of the hollow needle 12 is attached a disk-shaped gripping portion 13. An upper opening of the hollow needle 12 opens in the top surface of the gripping portion 13. On the lateral sides of the gripping portion 13 are fixed skirts 14, 15 extending downward. The skirts 14, 15 are provided for facilitating manual operation of the jig 11.

In the vicinity of the tip end of the hollow needle 12, a plurality of vanes 12a, and 12b are provided. The vanes 12a and 12b are designed to have a shape that approaches the hollow needle 12 as they extend to their tip ends, and have latch faces 12a1 and 12b1 at their upper ends, respectively. Owing to the above shape, the piercing resistance at the time of piercing the plug member 5 with the hollow needle 12 is not so large, and a large through hole is formed in the plug member 5 by the above vanes 12a and 12b. Furthermore, since the latch faces 12a1 and 12b1 are provided, it is possible to easily remove the plug member 5 and the sample collection part 3 together with the jig 11 from the sample storage part 2 after completion of filtration. More specifically, when the latch faces 12a1 and 12b1 are brought into abutment on the lower surface of the plug member 5, it is possible to securely drawn out the plug member 5 and the sample collection part 3 together with the jig 11 only by drawing out the jig 11 upward.

Figure 3:
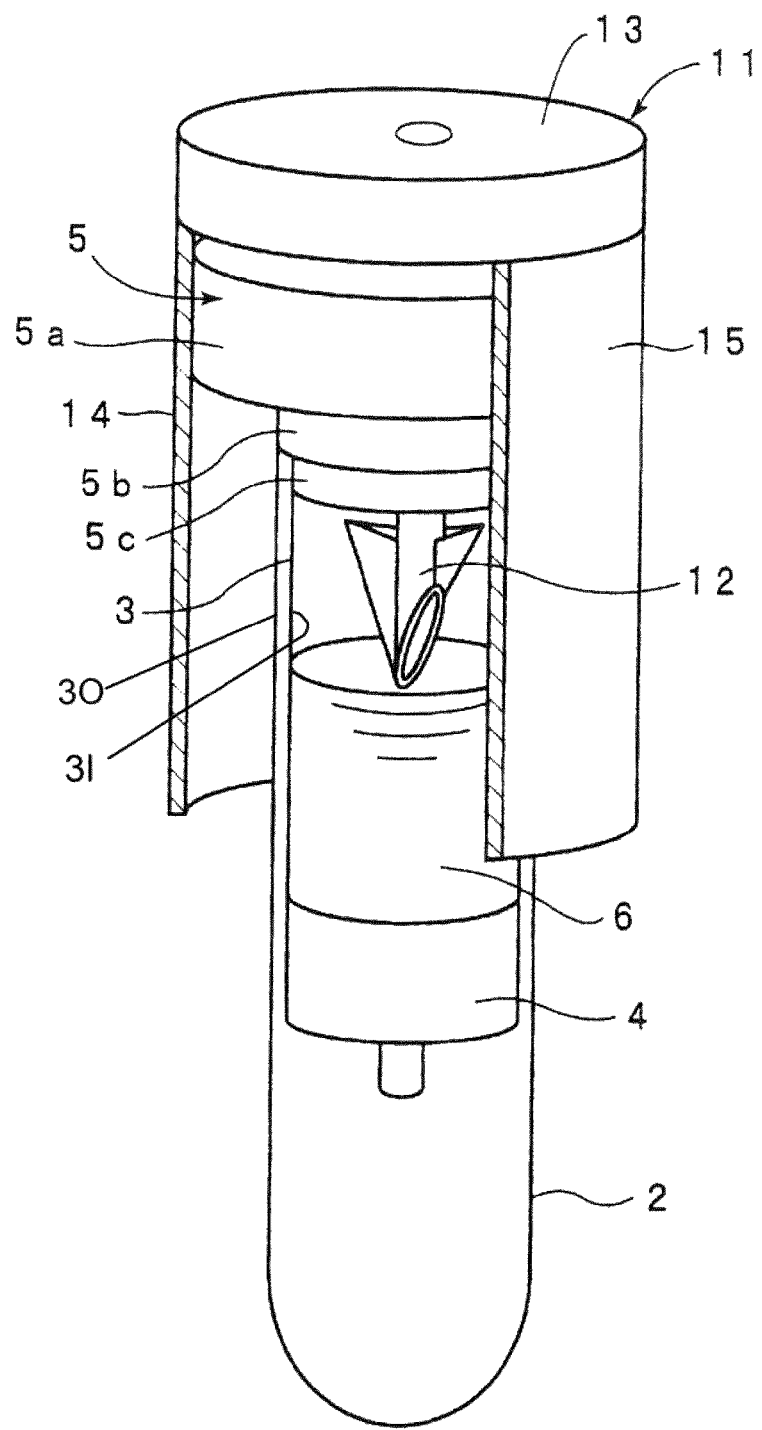
FIG. 3 is a schematic perspective view for explaining a process of resuming filtration by using the jig shown in FIG. 2.

Referring to FIG. 3, a filtering method using the jig 11 will be explained.

FIG. 3 is a schematic perspective view showing the state that the jig 11 is attached to the sample collecting container 1 in the progressive process of filtration after collecting blood in the sample collection part 3 by means of the aforementioned vacuum blood collection needle. As described above, the filtration may possibly stop during the process only by the remaining pressure in the sample collecting container 1. For dealing with this situation, the gripping portion 13 and the skirts 14 and 15 are gripped with a hand, and the plug member 5 is pierced with the hollow needle 12 serving as a communication needle when filtration stops. In this case, the hollow needle 12 is positioned so that the tip end of the hollow needle 12 locates above the blood 6 within the sample collection part 3. As a result of this, communication between the space in the sample collection part 3 and the atmosphere is established. Consequently, the pressure difference between upside and downside of the filter member 4 increases to allow progression of the filtration again. In this manner, filtration by the filter member 4 is securely completed.

Figure 4:
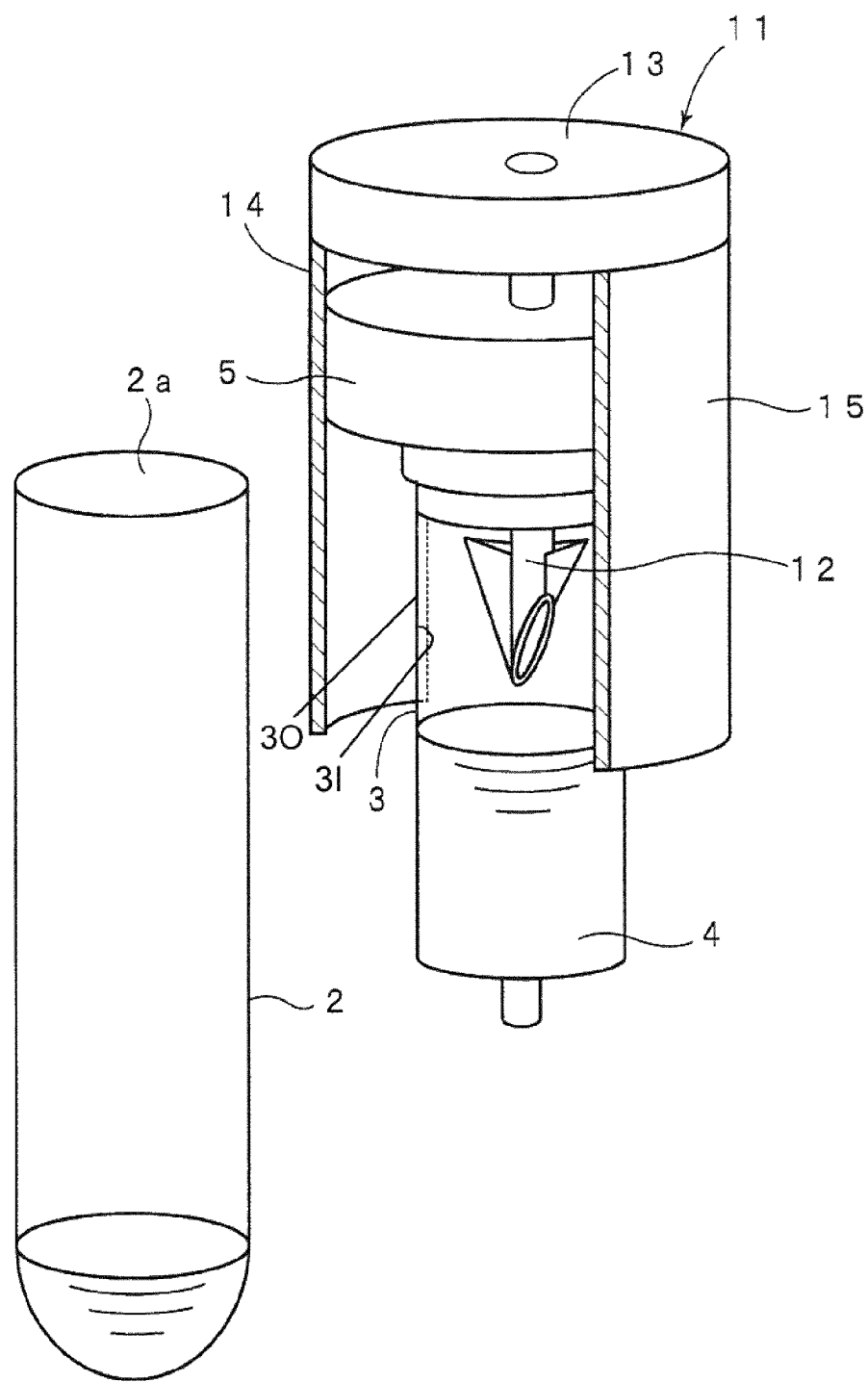
FIG. 4 is a schematic perspective view showing the state that the jig is removed from the sample storage part together with the plug member and the sample collection part after completion of filtration following the operation of FIG. 3.

After completion of the filtration, the jig 11 is gripped with a hand, and the plug member 5 and the sample collection part 3 are drawn out from the sample collecting container 1 together with the jig 11 (see FIG. 4). In this manner, it is possible to obtain the sample storage part 2 storing a filtered sample. The sample storage part 2 can be directly subjected to an automatic analyzer or the filtered sample in the sample storage part 2 may be collected by a dropper, a pipette or the like.

As described above, in the above filtering method according to the present embodiment, when filtration stops during the process because only the remaining pressure in the sample collecting container is relied on, it is possible to resume and continue filtration and filter the blood completely through the filter member 4 by using the hollow needle 12 of the jig 11. It is advantageous that filtration can be continued only by attaching the jig 11 to the sample collecting container 1 as described above and the plug member 5 does not need to be detached. Therefore, it is possible to avoid the possibility that the blood adheres to the operator to cause infection. Furthermore, since the space above the sample collection part 3 will not be opened, contamination by foreign matters will not occur.

Figure 5:
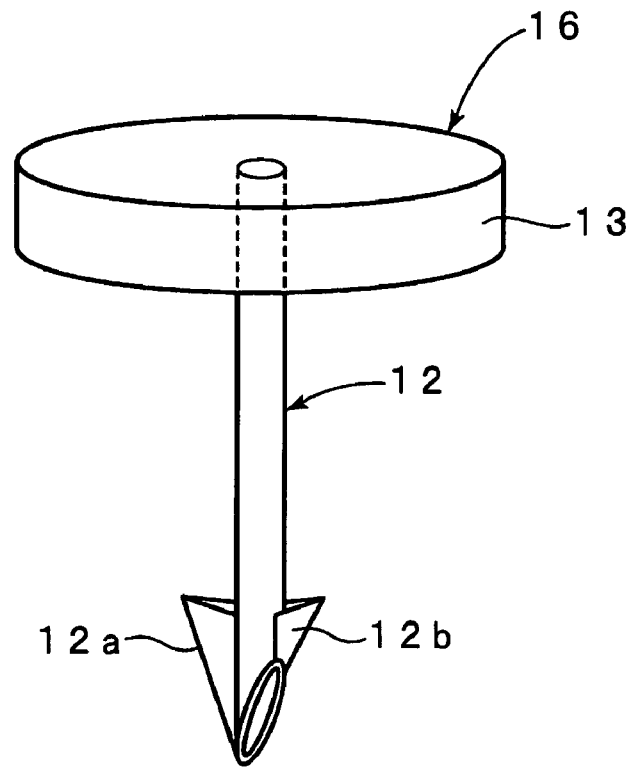
FIG. 5 is a perspective view of a jig used in a modified example of the first embodiment.

FIG. 5 is a schematic perspective view showing a modified example of the jig 11. A jig 16 shown in FIG. 5 is not provided with the skirts 14 and 15 shown in FIG. 2. As is the present example, the skirts 14 and 15 are not essential, and the jig 16 may consists exclusively of the gripping portion 13 and the hollow needle 12.

Figure 6:
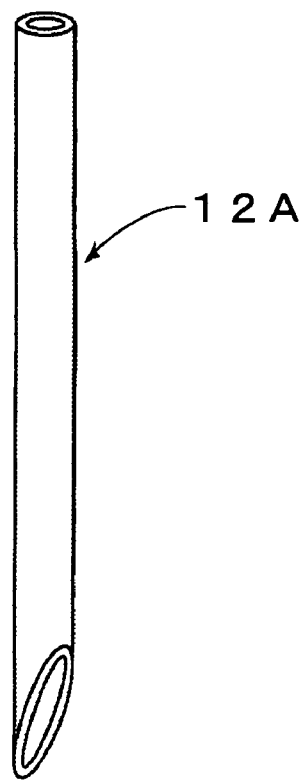
FIG. 6 is a perspective view of a hollow needle used in another modified example of a filtering method of the first embodiment.

Furthermore, as the communication needle, only a hollow needle 12A may be used as is the case of the hollow needle 12A shown in FIG. 6. In this case, the hollow needle 12A can be a longer one so that the hollow needle itself can be gripped with a hand and caused to pierce the plug member 5.

In the above first embodiment, the hollow needle as explained above is used as a communication needle for allowing communication between the interior and the exterior of the sample collecting container after filtration, however, in the present invention, communication needles other than hollow needles having a hollow flow channel can also be used.

Figure 12:
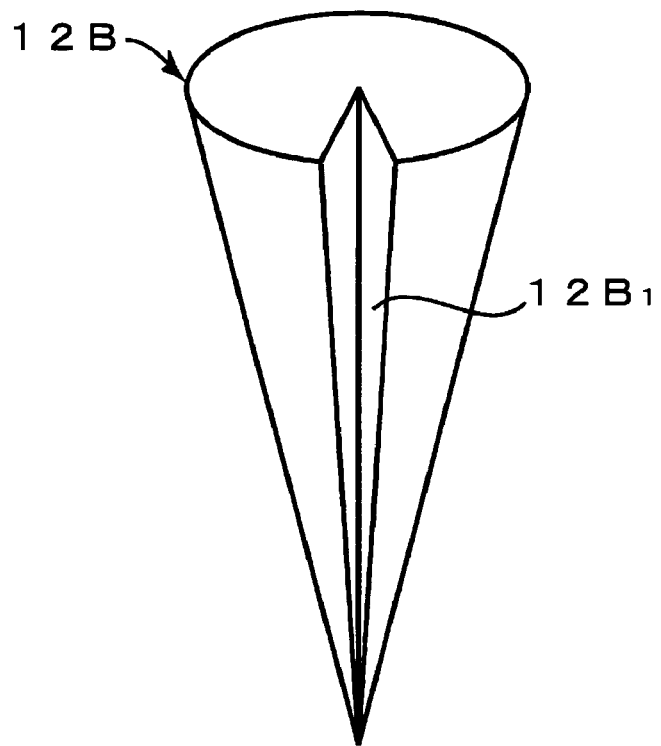
FIGS. 12A and 12B each represent a perspective view of a modified example of a communication needle used in the present invention.
Figure 12:
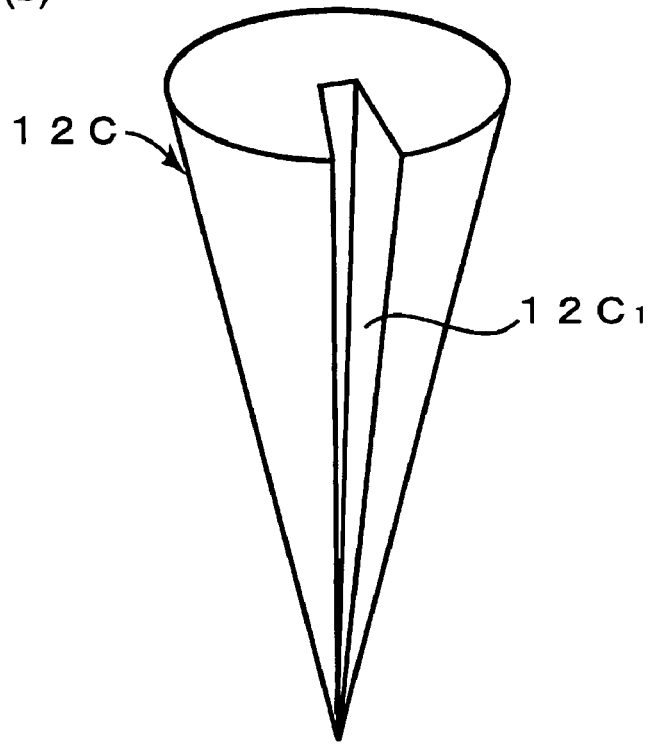

FIGS. 12A and 12B each represent a perspective view showing a modified example of such communication needles.

A communication needle 12B has a communicating groove 12B₁ extending from its needlepoint to an end opposite to the needlepoint. The communicating groove 12B₁ serving as a communicating flow channel is formed on the outer periphery of the communication needle 12B and has a generally fan-like cross section. One end of the communicating groove 12B₁ reaches the needlepoint. Therefore, by using the communication needle 12B in place of the hollow needle 12 in the sample collecting container 1 used in the first embodiment, for example, it is possible to establish communication between the internal space of the sample collection part and the atmosphere. Accordingly, the communicating groove 12B₁ does not necessarily reach the end opposite to the needlepoint insofar as it is long enough to establish communication between outside of the plug member 5 and inside of the sample collecting container.

A communication needle 12C shown in FIG. 12B is structured in a similar manner as the communication needle 12B except that the cross section shape of a communicating groove 12C₁ is generally trapezoidal in the communication needle 12C. The cross section shape of the communicating groove may be arbitrarily changed as described above.

Also a communication needle having a plurality of communicating grooves may be used.

Figure 7:
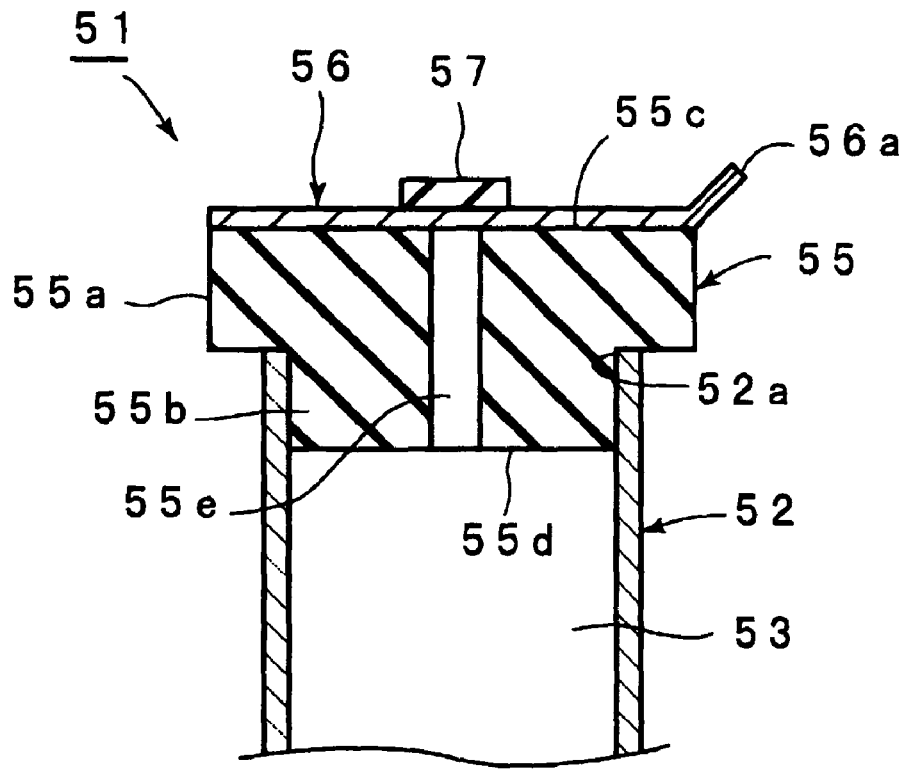
FIG. 7 is a partially cut away front section view of a sample collecting container according to a second embodiment.

FIG. 7 is a partially cutaway front section view for explaining a sample collecting container according to a second embodiment of the present invention.

In a sample collecting container 51, a cylindrical tube 52 having a bottom is used. Upper part of the tube 52 which constitutes a sample collection part 53 is illustrated. Although omitted in the FIG. 7, a filter member is disposed in a lower part of the sample collection part 53 and a space under the filter member of the tube constitutes a sample storage part.

The filter member can be formed of a material similar to those recited in the first embodiment. Also the tube 52 can be formed of a material similar to those forming the sample storage part 2 and the sample collection part 3 in the first embodiment.

In the sample collecting container according to the present embodiment, a plug member 55 has a gripping portion 55a and a press-in portion 55b. The press-in portion 55b is designed to hermetically seal an opening 52a of the tube 52.

The plug member 55 is formed of an appropriate elastic material such as rubber or elastomer.

The plug member 55 is formed with a through hole 55e extending from a top surface 55c to a bottom surface 55d. On the top surface 55c of the plug member 55, a sheet 56 serving as a sealing member is stuck. The sheet 56 is adhered or welded onto the top surface 55c of the plug member 55 so as to hermetically seal the through hole 55e. The sheet 56 can be formed of any appropriate material such as a laminate of aluminum foil and synthetic resin insofar as hermetical sealing is ensured.

On the top surface of the sheet 56, a reinforcing layer 57 is stuck. The reinforcing layer 57 is provided for preventing the sheet 56 from tearing by pressure difference between the internal pressure of the sample collecting container 51 and the atmosphere. Therefore, the reinforcing layer 57 is not necessarily provided when the sheet 56 has enough strength.

At one end of the sheet 56 is formed a notch 56a. The notch 56a projects outward than the top surface 55c of the plug member 55. By gripping the notch 56a with a hand, it is possible to easily peel the sheet 56 from the plug member 55.

The plug member 55 is usually pressed into an opening at the upper end of the tube 52, however, in the plug member according to the present invention, the plug member is not necessary pressed in insofar as it can close the opening. For example, the plug member 55 may be formed from a flexible sheet that is attached so as to seal the opening 52a of the tube 52. In this case, a through hole for establishing communication between inside and outside is formed in a part of the sheet-like plug member as described above and the through hole can be sealed with a sealing member attached to the outer surface of the plug member.

In the sample collecting container 51, the interior of the tube 52 is depressurized in advance.

Therefore, as is of the same with the first embodiment, a sample such as blood can be collected into the sample collection part 53 by using a vacuum blood collection needle. In the present case, the vacuum blood collection needle pierces the reinforcing layer 57 and extends into the sample collection part 53.

After collection of the sample, the vacuum blood collection needle is removed. Then the sample is filtered by a pressure difference between the sample collection part 53 and the space under the filter member disposed below which is not shown in the drawing. Also in the present embodiment, there is a fear that filtration stops during the process when the internal pressure of the tube 52 reaches equilibrium. In the present embodiment, when such a situation occurs, the through hole 55e is allowed to communicate with the atmosphere by picking the notch 56a with fingers and peeling off the sheet 56 from the plug member 55. As a result of this, the space over the filter member is allowed to communicate with the atmosphere, so that filtration resumes by the pressure difference between the downside space and the upside space of the filter member.

Thus, filtration canal so be securely accomplished without removing the plug member 55 from the tube 52 when the sample collecting container 51 is used.

Figure 8:
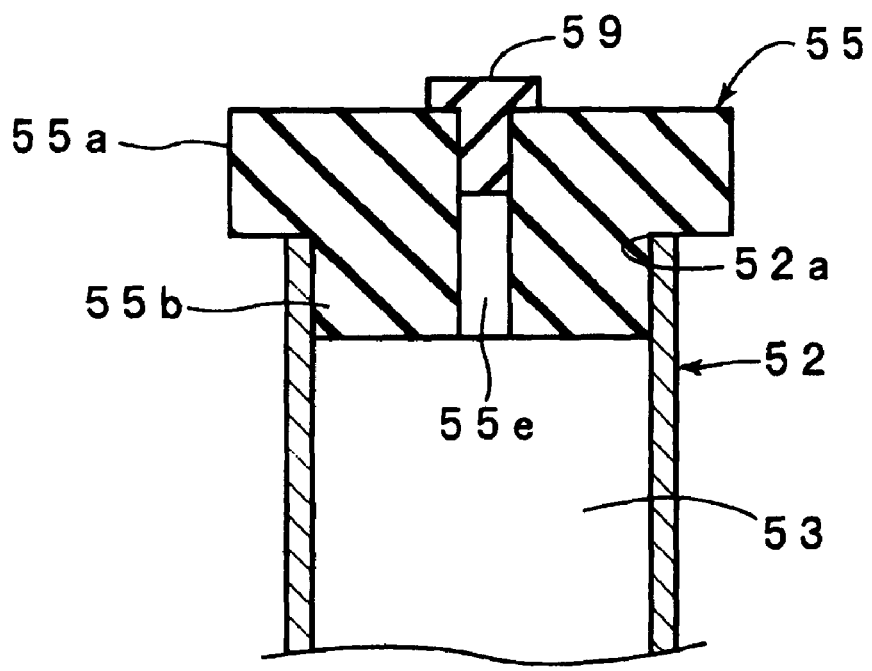
FIG. 8 is a partially cutaway front section view for explaining a modified example of the sample collecting container shown in FIG. 7.

FIG. 8 is a schematic front section view showing a modified example of the sample collecting container 51. In the sample collecting container 51, the sheet 56 is used as a sealing member for resuming filtration, however, a plug 59 that closes the through hole 55e may also be used. The plug 59 is formed of an elastic material such as rubber or elastomer, and initially pressed into the through hole 55e to hermetically seal the upper end of the through hole 55e. In collecting a sample with a vacuum blood collection needle, the center of the plug 59 may be pierced, or the plug member 55 may be pierced with a vacuum blood collection needle in some part other than the part where the plug 59 is provided.

Figure 9:
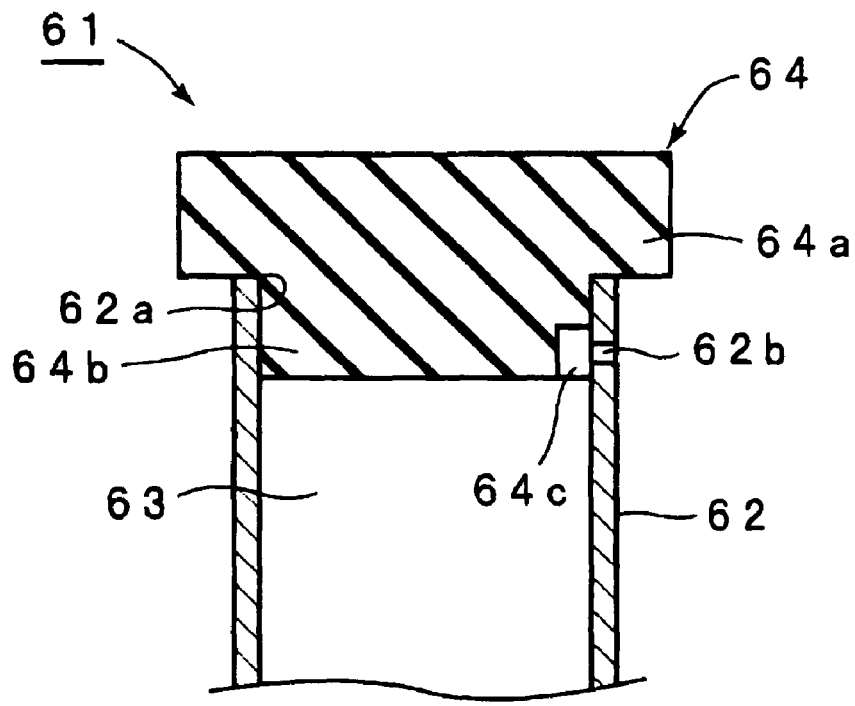
FIG. 9 is a partially cutaway front section view of a sample collecting container according to a third embodiment.

FIG. 9 is a partially cutaway schematic front section view for explaining a sample collecting container according to a third embodiment of the present invention. In a sample collecting container 61, a tube 62 having a bottom and an opening 62a at its upper end is used. In the tube 62, a filter member (not illustrated) is located at a middle height position, and the space over the filter member constitutes a sample collection part 63 and the space under the filter member constitutes a sample storage part.

A plug member 64 is pressed into the tube so as to hermetically seal the opening 62a at the upper end of the tube 62. The plug member 64 includes a gripping portion 64a and a press-in portion 64b which is smaller in diameter than the gripping portion 64a. The press-in portion 64b is a portion to be pressed into the tube 62.

The press-in portion 64b is formed with a recess 64c in a part of the outer periphery. In the tube wall of the tube 62 is formed a through hole 62b that penetrates through the tube wall from inside to outside. The through hole 62b is formed in such a manner that a flow channel that establishes communication between the sample collection part 63 and the atmosphere is formed by the recess 64c when the circumferential position of the recess 64c coincides with that of the through hole 62b.

More specifically, in the condition illustrated in FIG. 9, the recess 64c and the through hole 62b are aligned in the circumferential direction to form the flow charnel, however there are initially in different positions. That is, initially the recess 64c is at a position not aligning with the through hole 62b so as to keep the depressurized condition in the tube 62. Therefore, as is the cases of the first and the second embodiments using the sample collecting containers 1 and 11, it is possible to collect a liquid sample such as blood into the sample collection part 63 with a vacuum blood collection needle by utilizing the reduced pressure in the through hole 62b.

Then a sample such as blood is filtered by using a filter member in the similar manner as the first and the second embodiments. In this case filtration stops during the process when the pressures of the upside space and the downside space of the filter member reach equilibrium. When such a situation occurs, the plug member 64 is rotated so that the through hole 62b is opposite to the recess 64c as shown in FIG. 9 by shifting the plug member 64 circumferentially. Only with this operation, the flow channel is formed and communication between the sample collection part 63 and the atmosphere is established, so that pressure difference generates between the sample collection part 63 and the sample storage portion under the filter member again to allow progression of filtration. And in the same manner as the case of the first and the second embodiments, filtration of sample is securely completed.

Figure 10:
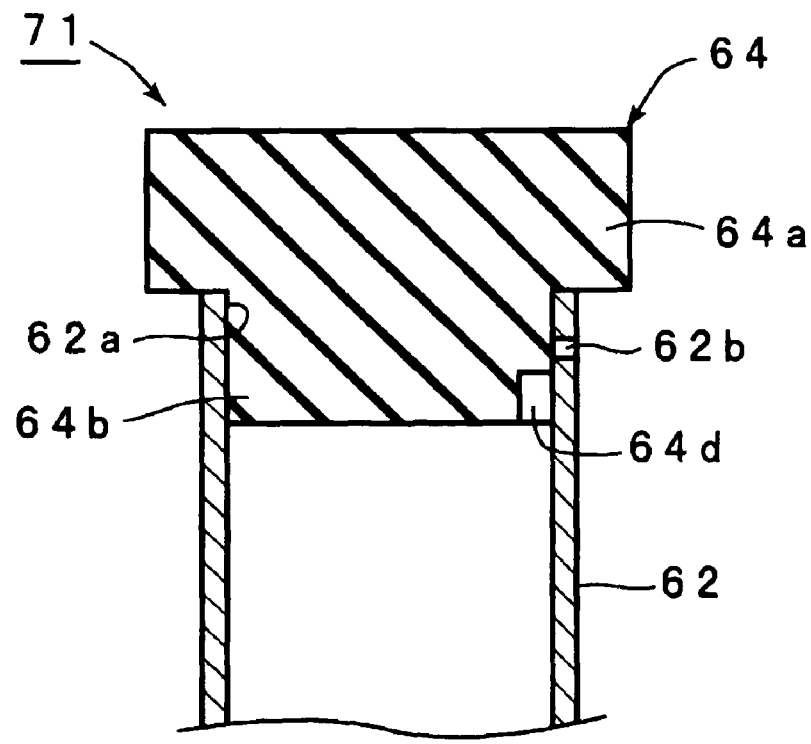
FIG. 10 is a partially cutaway front section view of a sample collecting container according to a fourth embodiment.

FIG. 10 is a partially cutaway front section view of a sample collecting container according to a fourth embodiment of the present invention. A sample collecting container 71 is structured in the same manner as the sample collecting container 61 of the third embodiment except for an arrangement for resuming filtration. Therefore, explanation will be given for the parts that are different from those of the third embodiment.

In the sample collecting container 71, the through hole 62b is provided in the tube 62. On the other hand, a recess 64d is formed in the press-in portion 64b of the plug member 64. The recess 64d is provided at a position lower than the through hole 62b as shown in FIG. 10. Initially, the sample collection part 63 is cut off from the atmosphere because the recess 64d and the through hole 62b are misaligned in the longitudinal direction of the tube 62 as shown in FIG. 10.

When the filtration stops during the process because of the operation as described above, the plug member 64 in the state shown in FIG. 10 is slightly drawn out upward. As a result of this, the through hole 62b comes into opposite to the recess 64d, so that the sample collection part 63 is allowed to communicate with the atmosphere. In brief, in the sample collecting container 71, filtration can be resumed by slightly drawing out the plug member 64 upward.

Therefore, also in the case of using the sample collecting container 71, the plug member 64 does not need to be detached from the tube 62, so that the operator is less likely to acquire infection through blood and contamination by foreign matters is less likely to occur in the sample collection part 63.

Figure 11:
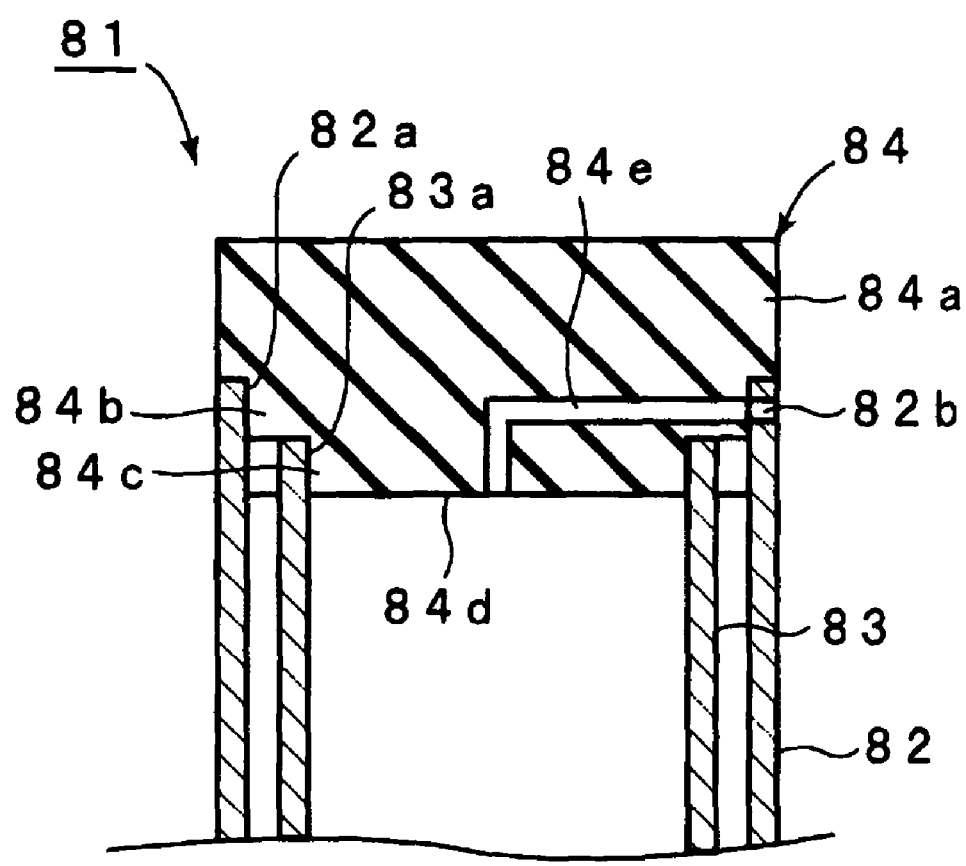
FIG. 11 is a partially cutaway front section view of a sample collecting container according to a fifth embodiment.

FIG. 11 is a schematic front section view for explaining a sample collecting container according to a fifth embodiment of the present invention.

In a sample collecting container 81, a sample collection part 83 of cylindrical shape is inserted into a sample storage part 82 implemented by a tube having a bottom. The sample storage part 82 and the sample collection part 83 are structured in the similar manner as the sample storage part 2 and the sample collection part 3 of the first embodiment. Concretely, although not shown in the drawing, a filter member is accommodated in a lower part of the sample collection part 83. And the space under the sample storage part 82 will store a sample having experienced filtration.

The plug member 84 includes a gripping portion 84a, a larger-diameter portion 84b and a smaller-diameter portion 84c. The sample storage portion 82 is hermetically sealed by the larger-diameter portion 84b, and an opening at the upper end of the sample collection part 83 is hermetically sealed by the smaller-diameter portion 84c.

In the present embodiment, an arrangement that resumes filtration when filtration stops during the process in the sample collecting container 81 is provided in the plug member 84 and the sample storage part 82. Concretely, a through hole 82b is formed at a position slightly lower than an opening 82a at the upper end of the sample storage part 82. The through hole 82b is formed in a part of inner surface that contacts the larger-diameter portion 84b.

On the other hand, the plug member 84 is formed with a flow channel 84e which is open to the outer peripheral surface of the larger-diameter portion 84b at its one end and open to a bottom surface 84d of the plug member 84 at its other end. The vertical position of the opening which is open to the larger-diameter portion 84b in the flow channel 84e generally coincides with that of the through hole 82b of the sample storage part 82.

Therefore, when the filtration stops during the process, the sample collection part can be allowed to communicate with the atmosphere by establishing communication between the flow channel 84e and the through hole 82b as shown in the drawing by rotation of the plug member 84. Therefore, filtration can be resumed and filtration of a sample such as blood can be securely completed as is the same with the first to the fourth embodiments.

Also in this embodiment, blood is less likely to adhere to fingers of the operator during the operation for resuming filtration, and contamination by foreign matters is less likely to occur in the sample collection part.

In the sample filtering method using the sample collecting container according to the first embodiment, the sample collecting container 1 having a double tube structure as described above is used, however, the sample filtering method may be applied to the cases where sample collecting containers disclosed in Japanese Unexamined Patent Publication No. 2002-277357, Japanese published Patent No. 3015854, Japanese Unexamined Patent Publication No. 11-290297 (1999), Japanese Unexamined Patent Publication No. 4-20856 (1992) and Japanese Unexamined Patent Publication No. 2001-321365 are used without being limited to the case using the aforementioned sample collecting container. The filtering method of the first embodiment may also be applied to the cases where the sample collecting containers of the second to the fifth embodiments are used.

Furthermore, the sample collecting containers according to the second to the fifth embodiments of the invention are featured by an arrangement for resuming filtration as described above, and structures other than this arrangement can be arbitrarily changed. For example, sample collecting containers disclosed in Japanese Unexamined Patent Publication No. 2002-277357, Japanese published Patent No. 3015854, Japanese Unexamined Patent Publication No. 11-290297 (1999), Japanese Unexamined Patent Publication No. 4-20856 (1992) and Japanese Unexamined Patent Publication No. 2001-321365 can also adopt the filtration resuming arrangements according to the second to the fifth embodiments.

INDUSTRIAL APPLICABILITY

In the sample filtering method using a sample collecting container according to the first aspect of the invention, even when the filtration stops during the process, it is possible to resume filtration by piercing the plug member with a hollow needle to allow communication between the sample collection part and the outside. Therefore, filtration of a liquid sample such as blood can be securely conducted and the plug member does not need to be removed entirely. Therefore, the operator is less likely to be infected through blood and contamination of the sample by foreign matters is less likely to occur.

The jig according to the second aspect of the present invention is used to establish communication between inside and outside of a plug member of a sample collecting container and can be used in various aspects. For example, it is suitably used for establishing communication between inside and outside of the sample collecting container in the sample filtering method according to the first aspect of the invention. Concretely, only by gripping the jig with a hand via the gripping portion and the skirts and piercing a plug member of the sample collecting container with a hollow needle, it is possible to establish communication between inside and outside of the plug member. In addition, since the vanes are formed as described above, it is possible to detach the plug member together with the jig from the sample collecting container when detaching the jig.

Also in the sample collecting container according to the third aspect of the invention, since filtration is resumed by removal of the sealing member, the operator is less likely to be infected by adhesion of the blood and contamination of the sample by foreign matters is less likely to occur.

In the sample collecting container according to the fourth aspect of the invention, filtration is resumed by communication of the through hole provided in the sample collection part and the flow channel provided in the plug member. Therefore, filtration can be resumed without removing the plug member as is the same with the first to the third aspects of the invention.

Also in the sample collecting container according to the fifth aspect of the invention, when the plug member is drawn out while keeping hermetical sealing with the inner surface of the sample collection part, the through hole provided in the sample collection part and the flow channel of the plug member are brought into communication with each other. Consequently, filtration can be resumed without detaching the plug member.

Therefore, also in the fourth and the fifth aspects of the present invention, filtration can be resumed without detaching the plug member, the operator is less likely to be infected by adhesion of the blood and contamination of the sample by foreign matters is less likely to occur.

Therefore, according to the first to the fifth aspects of the invention, it is possible to filter a liquid sample safely and reliably.

The invention claimed is:

1. A method for filtering a sample using a sample collecting container that includes:
   a sample collection part storing a collected liquid sample and having an opening;
   a plug member provided so as to hermetically seal the opening;
   a filter member provided in the sample collection part, for filtering the sample collected in the sample collection part; and
   a sample storage part for storing a sample filtered by the filter member, the internal pressure thereof being reduced in advance,
   wherein after collecting a sample in the sample collection part using a vacuum blood collection needle, the sample is filtered by a pressure difference between the sample collection part and the sample storage part, while the plug member is pierced by a communication needle having a communication flow channel to establish communication between the sample collection part and the exterior, thereby elevating the internal pressure of the sample collection part,
   wherein a communication between an internal space of the sample collection part and atmosphere occurs (1) after collecting the sample in the sample collection part and (2) due to the piercing of the plug member by the communication needle having the communication flow channel.

2. The method for filtering a sample according to claim 1, wherein the communication needle is a hollow needle.

3. The method for filtering a sample according to claim 1, wherein the communication needle has a communication groove formed on its outer surface and the communication groove extends from a needlepoint toward an end opposite to the needlepoint.

4. A sample collecting container that enables filtration of a liquid sample, comprising:
   a sample collection part having an opening and storing a collected liquid sample;

a plug member pressed into the opening so as to hermetically seal the opening;
a filter member provided in the sample collection part, for filtering the sample collected in the sample collection part; and
a sample storage part for storing the sample filtered by the filter member,
the sample collection part, the filter member and the sample storage part being hermetically connected with each other and the internal pressure of sample storage part being reduced in advance,
wherein an open through hole is formed in a part of inner surface of the sample collection part that is in contact with the plug member, and a flow channel is formed in a part of outer surface of the plug member contacting the inner surface of the sample collection part, the flow channel establishing communication between the through hole and the interior of the sample collection part when its circumferential position is brought into coincidence with the through hole.

* * * * *